US012068079B2

United States Patent
Sankaran et al.

(10) Patent No.: US 12,068,079 B2
(45) Date of Patent: *Aug. 20, 2024

(54) SYSTEMS AND METHODS FOR VIRTUAL CONTRAST AGENT SIMULATION AND COMPUTATIONAL FLUID DYNAMICS (CFD) TO COMPUTE FUNCTIONAL SIGNIFICANCE OF STENOSES

(71) Applicant: HeartFlow, Inc., Redwood City, CA (US)

(72) Inventors: Sethuraman Sankaran, Palo Alto, CA (US); Leo Grady, Millbrae, CA (US); Charles A. Taylor, Menlo Park, CA (US)

(73) Assignee: HeartFlow, Inc., Mountain View, CA (US)

(*) Notice: Subject to any disclaimer, the term of this patent is extended or adjusted under 35 U.S.C. 154(b) by 164 days.

This patent is subject to a terminal disclaimer.

(21) Appl. No.: 15/227,429

(22) Filed: Aug. 3, 2016

(65) Prior Publication Data

US 2016/0342765 A1    Nov. 24, 2016

Related U.S. Application Data

(63) Continuation of application No. 14/317,703, filed on Jun. 27, 2014, now Pat. No. 9,449,145.

(Continued)

(51) Int. Cl.
*G16H 50/30* (2018.01)
*A61B 5/00* (2006.01)
(Continued)

(52) U.S. Cl.
CPC ......... *G16H 50/30* (2018.01); *A61B 5/02007* (2013.01); *A61B 5/026* (2013.01);
(Continued)

(58) Field of Classification Search
CPC ........ G16H 50/30; G16H 50/50; G16H 10/60; G06F 19/3431; A61B 6/507; A61B 6/504;
(Continued)

(56) References Cited

U.S. PATENT DOCUMENTS 3,757,947 A * 9/1973 Wakefield .............. B01D 61/28
                                                        210/86
6,711,433 B1 * 3/2004 Geiger .................. G06T 11/008
                                                        378/98.12

(Continued)

OTHER PUBLICATIONS

Van de Hoef, Tim P., et al. "Physiological basis and long-term clinical outcome of discordance between fractional flow reserve and coronary flow velocity reserve in coronary stenoses of intermediate severity." Circulation: Cardiovascular Interventions 7.3 (2014): 301-311. (Mar. 2014) (Year: 2014).*

(Continued)

*Primary Examiner* — Akash Saxena
(74) *Attorney, Agent, or Firm* — Bookoff McAndrews, PLLC

(57) ABSTRACT

Systems and methods are disclosed for assessing a risk of disease. One method includes obtaining an anatomic model associated with a target anatomy; modeling, using a processor, an injection of one or more virtual contrast agents into the anatomic model; performing a simulation of flow of blood and the one or more virtual contrast agents through the anatomic model; and computing one or more characteristics of concentration associated with the one or more virtual contrast agents at one or more locations in the anatomic model based on the simulation.

17 Claims, 6 Drawing Sheets

Related U.S. Application Data

(60) Provisional application No. 61/982,580, filed on Apr. 22, 2014.

(51) Int. Cl.

| | |
|---|---|
| *A61B 5/02* | (2006.01) |
| *A61B 5/026* | (2006.01) |
| *A61B 6/00* | (2024.01) |
| *A61B 6/50* | (2024.01) |
| *G06T 19/00* | (2011.01) |
| *G06T 19/20* | (2011.01) |
| *G06V 20/20* | (2022.01) |
| *G16H 10/60* | (2018.01) |
| *G16H 50/50* | (2018.01) |
| *G16Z 99/00* | (2019.01) |

(52) U.S. Cl.
CPC ............ *A61B 5/7275* (2013.01); *A61B 6/481* (2013.01); *A61B 6/503* (2013.01); *A61B 6/504* (2013.01); *A61B 6/507* (2013.01); *G06T 19/20* (2013.01); *G16H 10/60* (2018.01); *G16H 50/50* (2018.01); *G16Z 99/00* (2019.02); *A61B 6/5217* (2013.01); *G06T 19/006* (2013.01); *G06T 2207/30048* (2013.01); *G06T 2207/30104* (2013.01); *G06T 2210/41* (2013.01); *G06V 20/20* (2022.01)

(58) Field of Classification Search
CPC ..... A61B 6/503; A61B 6/481; A61B 5/02007; A61B 5/026; A61B 5/7275; A61B 6/5217; G06T 2207/30048; G06T 2207/30104
USPC .......................................................... 703/20
See application file for complete search history.

(56) References Cited

U.S. PATENT DOCUMENTS

| | | | | |
|---|---|---|---|---|
| 8,315,812 | B2 | 11/2012 | Taylor | |
| 8,411,919 | B2* | 4/2013 | Kiraly | G06K 9/342 |
| | | | | 382/128 |
| 8,706,196 | B2 | 4/2014 | Redel | |
| 9,449,145 | B2* | 9/2016 | Sankaran | G06T 19/20 |
| 2005/0020929 | A1* | 1/2005 | Murphy | G06F 18/00 |
| | | | | 600/509 |
| 2005/0065432 | A1* | 3/2005 | Kimura | A61B 5/0263 |
| | | | | 600/420 |
| 2007/0053555 | A1* | 3/2007 | Ooi | A61B 6/461 |
| | | | | 382/128 |
| 2008/0286735 | A1* | 11/2008 | Cusano | G09B 23/30 |
| | | | | 434/267 |
| 2008/0294038 | A1* | 11/2008 | Weese | A61B 6/507 |
| | | | | 600/431 |
| 2010/0004526 | A1* | 1/2010 | Wei | A61P 25/28 |
| | | | | 600/407 |
| 2010/0130878 | A1 | 5/2010 | Lasso | |
| 2011/0002517 | A1 | 1/2011 | Mollus et al. | |
| 2012/0041739 | A1 | 2/2012 | Taylor | |
| 2012/0243761 | A1 | 9/2012 | Senzig | |
| 2013/0028494 | A1* | 1/2013 | Groth | G06T 7/0012 |
| | | | | 382/130 |
| 2013/0085774 | A1 | 4/2013 | Chen | |
| 2013/0324842 | A1* | 12/2013 | Mittal | A61B 6/5217 |
| | | | | 600/431 |
| 2014/0073977 | A1* | 3/2014 | Grady | A61B 5/021 |
| | | | | 600/504 |
| 2014/0088414 | A1* | 3/2014 | Mittal | G06T 7/0016 |
| | | | | 600/425 |
| 2014/0200867 | A1* | 7/2014 | Lavi | G16H 30/20 |
| | | | | 703/2 |
| 2015/0100572 | A1* | 4/2015 | Kalafut | G16H 10/40 |
| | | | | 707/736 |
| 2015/0302139 | A1* | 10/2015 | Sankaran | G16H 50/50 |
| | | | | 703/20 |

OTHER PUBLICATIONS

Makhijani, Vinod B.; Yang, H. Q.; Dionne, Paul J.; Thubrikar, Mano J.‡. Three-Dimensional Coupled Fluid-Structure Simulation of Pericardial Bioprosthetic Aortic Valve Function. ASAIO Journal 43(5):p M392, Sep. 1997. (Year: 1997).*

Zhang JM, Zhong L, Luo T, Huo Y, Tan SY, Wong AS, Su B, Wan M, Zhao X, Kassab GS, Lee HP, Khoo BC, Kang CW, Ba T, Tan RS. Numerical simulation and clinical implications of stenosis in coronary blood flow. Biomed Res Int. 2014;2014:514729. doi: 10.1155/2014/514729. Epub Jun. 2, 2014. (Year: 2014).*

Qi Sun et al.: "Quantitative evaluation of virtual angiography for interventional X-ray acquisitions", Biomedical Imaging: From Nano to Macro, 2009. ISBI '09. IEEE International Symposium on, IEEE, Piscataway, NJ, USA, Jun. 28, 2009 (Jun. 28, 2009), pp. 895-898.

International Preliminary Report on Patentability for corresponding Application No. PCT/US2015/026750 dated Oct. 25, 2016, (8 pages).

Benjamin J. W. Chow et al., "Can Differences in Corrected Coronary Opacification Measured With Computed Tomography Predict Resting Coronary Artery Flow", Journal of the American College of Cardiology, vol. 57, No. 11, 2011, pp. 1280-1288.

Jin-Ho Choi, et al., "Diagnostic Performance of Intracoronary Gradient-based Methods by Coronary Computed Tomography Angiography for the Evaluation of Physiologically Significant Coronary Artery Stenoses: a validation study with fractional flow reserve", European Heart Journal—Cardiovascular Imaging (2012), 13, pp. 1001-1007.

Makoto Yamashita et al., "Noninvasive Evaluation of Coronary Reperfusion by CT Angiography in Patients with STEMI", JACC 2013, JACC: Cardiovascular Imaging, vol. 4, No. 2, 2011. pp. 141-149.

A J Oude Ophius et al., "Angiographic Assessment of Prospectively Determined non-invasive reperfusion indices in acute Myocardial Infarction", Heart 2000, Heart 2000, 84, pp. 164-170.

Lee et al., "Noninvasive Evaluation of Coronary Reperfusion by Transthoracic Doppler Echocardiography in Patients With Anterior Acute Myocardial Infarction Before Coronary Intervention", Circulation 2003. pp. 2763-2768.

Endres, Jurgen, et al. "A Workflow for Patient-Individualized Virtual Angiogram Generation Based on CFD Simulation" Computational & Mathematical Methods in Medicine (2012).

Khokhar, Usman, et al. "Automated Coronary Plaque and Stenosis Assessment on Coronary CT Angiography: A Closer Look at Coronary Atherosclerosis" Current Cardiovascular Imaging Reports, vol. 6, iss. 3, pp. 292-299 (Feb. 2013) available at <http://link.springer.com/article/1 0.1 007/s1241 0-013-9194-4>.

Einstein, Andrew J. "TAG—Is It It ?: Improving Coronary Computed Tomography Angiography With the Isotemporal Transluminal Contrast Attenuation Gradient" Cardiac Imaging: Editorial Comment, vol. 61, issue 12 (Mar. 2013) available from <http://content.onlinejacc.org/article.aspx?articleid=1653043>. (continued from U above) at <http://ehjcimaging.oxfordjournals.org/content!ejechocard/13/12/1 001.full.pdf>.

Choi, Jin-Ho, et al. "Diagnostic performance of intracoronary gradient-based methods by coronary computed tomography angiography for the evaluation of physiologically significant coronary artery stenoses: a validation study with fractional flow reserve" European Heart J. -Cardiovascular Imaging, vol. 13, pp. 1001-1007 (2012) available.

Koo, Bon-Kwon, et al. "Diagnosis of Ischemia-Causing Coronary Stenoses by Noninvasive Fractional Flow Reserve Computed From Coronary Computed Tomographic Angiograms" J. Am. College Cardiology, vol. 58, No. 19, pp. 1989-1997 (2011 ).

(56) References Cited

OTHER PUBLICATIONS

Min, James, et al. "Diagnostic Accuracy of Fractional Flow Reserve From Anatomic CT Angiography" J. Am. Med. Ass., vol. 308, No. 12, pp. 1237-1245(2012).
Wasilewski, Jaroslaw, et al. "Invasive and non-invasive fractional flow reserve index in validation of hemodynamic severity of intracoronary lesions" Postep Kardiol. Inter., 9, 2 (32), pp. 160-169 (2013) available from <http://www.termedia.pi/Journal/-35/Streszczenie-20896>.
Hlatky, Mark, et al. "Projected Costs and Consequences of Computed Tomography-Determined Fractional Flow Reserve" Clinical Cardiology, vol. 36, No. 12, pp. 743-748 (2013).
Min, James, et al. "Usefulness of Noninvasive Fractional Flow Reserve Computed from Coronary Computed Tomographic Angiograms for Intermediate Stenoses Confirmed by Quantitative Coronary Angiography" Am. J. Cardiology, vol. 110, issue 7, pp. 971-976 (2012) available from <http://www.sciencedirect.com/science/article/pii/S0002914912014348>.
Zhang, Jun-Mei, et al. "Area Stenosis Associated with Non-Invasive Fractional Flow Reserve Obtained from Coronary CT Images" IEEE 35th AnnualInt'l Conf. EMBS, pp. 3865-3868 (2013).
Wong, Dennis, et al. "Transluminal Attenuation Gradient in Coronary Computed Tomography Angiography Is a Novel Noninvasive Approach to the Identification of Functionally Significant Coronary Artery Stenosis: A Comparison With Fractional Flow Reserve" J. Am. College Cardiology, vol. 61, No. 12, pp. 1271-1279 (Mar. 2013).

\* cited by examiner

SYSTEMS AND METHODS FOR VIRTUAL CONTRAST AGENT SIMULATION AND COMPUTATIONAL FLUID DYNAMICS (CFD) TO COMPUTE FUNCTIONAL SIGNIFICANCE OF STENOSES

RELATED APPLICATION(S)

This application is a continuation of U.S. application Ser. No. 14/317,703, filed Jun. 27, 2014, which claims priority to U.S. Provisional Application No. 61/982,580 filed Apr. 22, 2014, all of which are hereby incorporated by reference herein in their entireties.

FIELD OF THE INVENTION

Various embodiments of the present disclosure relate generally to medical modeling and related methods. More specifically, particular embodiments of the present disclosure relate to systems and methods for modeling of blood flow rate using virtual contrast agents to compute metrics indicating functional significance of stenoses.

BACKGROUND

Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

A need exists to provide more accurate data relating to coronary lesions, e.g., size, shape, location, functional significance (e.g., whether the lesion impacts blood flow), etc. Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers).

For example, anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent. However, CCTA also cannot provide direct information on the functional significance of coronary lesions, e.g., whether the lesions affect blood flow. In addition, since CCTA is purely a diagnostic test, it can neither be used to predict changes in coronary blood flow, pressure, or myocardial perfusion under other physiologic states (e.g., exercise), nor can it be used to predict outcomes of interventions.

Thus, patients may require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, does not provide data for assessing the functional significance of coronary lesions. For example, a doctor may not be able to diagnose whether a coronary lesion is harmful without determining whether the lesion is functionally significant. Thus, CCA has led to a procedure referred to as an "oculostenotic reflex", in which interventional cardiologists insert a stent for every lesion found with CCA regardless of whether the lesion is functionally significant. As a result, CCA may lead to unnecessary operations on the patient, which may pose added risks to patients and may result in unnecessary heath care costs for patients.

During diagnostic cardiac catheterization, the functional significance of a coronary lesion may be assessed invasively by measuring the fractional flow reserve (FFR) of an observed lesion. FFR is defined as the ratio of the mean blood pressure downstream of a lesion divided by the mean blood pressure upstream from the lesion, e.g., the aortic pressure, under conditions of increased coronary blood flow, e.g., when induced by intravenous administration of adenosine. Blood pressures may be measured by inserting a pressure wire into the patient. Thus, the decision to treat a lesion based on the determined FFR may be made after the initial cost and risk of diagnostic cardiac catheterization has already been incurred.

To reduce the above disadvantages of invasive FFR measurements, methods have been developed for assessing coronary anatomy, myocardial perfusion, and coronary artery flow noninvasively. Specifically, computational fluid dynamics (CFD) simulations have been successfully used to predict spatial and temporal variations of flow rate and pressure of blood in arteries, including FFR. Such methods and systems benefit cardiologists who diagnose and plan treatments for patients with suspected coronary artery disease, and predict coronary artery flow and myocardial perfusion under conditions that cannot be directly measured, e.g., exercise, and to predict outcomes of medical, interventional, and surgical treatments on coronary artery blood flow and myocardial perfusion.

However, correlation between calculated functional significance of stenoses and conclusions given by experimental data may be improved. Therefore, a need exists to improve reliability of measurements for indicating functional significance of stenoses. More specifically, a need exists to improve measurements based on flow rates as means for determining functional significance of stenoses.

The foregoing general description and the following detailed description are exemplary and explanatory only and are not restrictive of the disclosure.

SUMMARY

According to certain aspects of the present disclosure, systems and methods are disclosed for assessing a risk of heart disease. One method includes: obtaining an anatomic model associated with a target anatomy; modeling, using a processor, an injection of one or more virtual contrast agents into the anatomic model; performing a simulation of flow of blood and the one or more virtual contrast agents through the anatomic model; and computing one or more characteristics of concentration associated with the one or more virtual contrast agents at one or more locations in the anatomic model based on the simulation.

In accordance with another embodiment, a system for assessing a risk of heart disease comprises: a data storage device storing instructions for assessing risk of heart disease; and a processor configured for: obtaining an anatomic model associated with a target anatomy; modeling, using a processor, an injection of one or more virtual contrast agents into the anatomic model; performing a simulation of flow of blood and the one or more virtual contrast agents through the anatomic model; and computing one or more characteristics of concentration associated with the one or more virtual contrast agents at one or more locations in the anatomic model based on the simulation.

In accordance with yet another embodiment, a non-transitory computer readable medium for use on a computer system containing computer-executable programming instructions for assessing a risk of heart disease is provided. The method includes: obtaining an anatomic model associated with a target anatomy; modeling, using a processor, an injection of one or more virtual contrast agents into the anatomic model; performing a simulation of flow of blood and the one or more virtual contrast agents through the anatomic model; and computing one or more characteristics of concentration associated with the one or more virtual contrast agents at one or more locations in the anatomic model based on the simulation.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1:
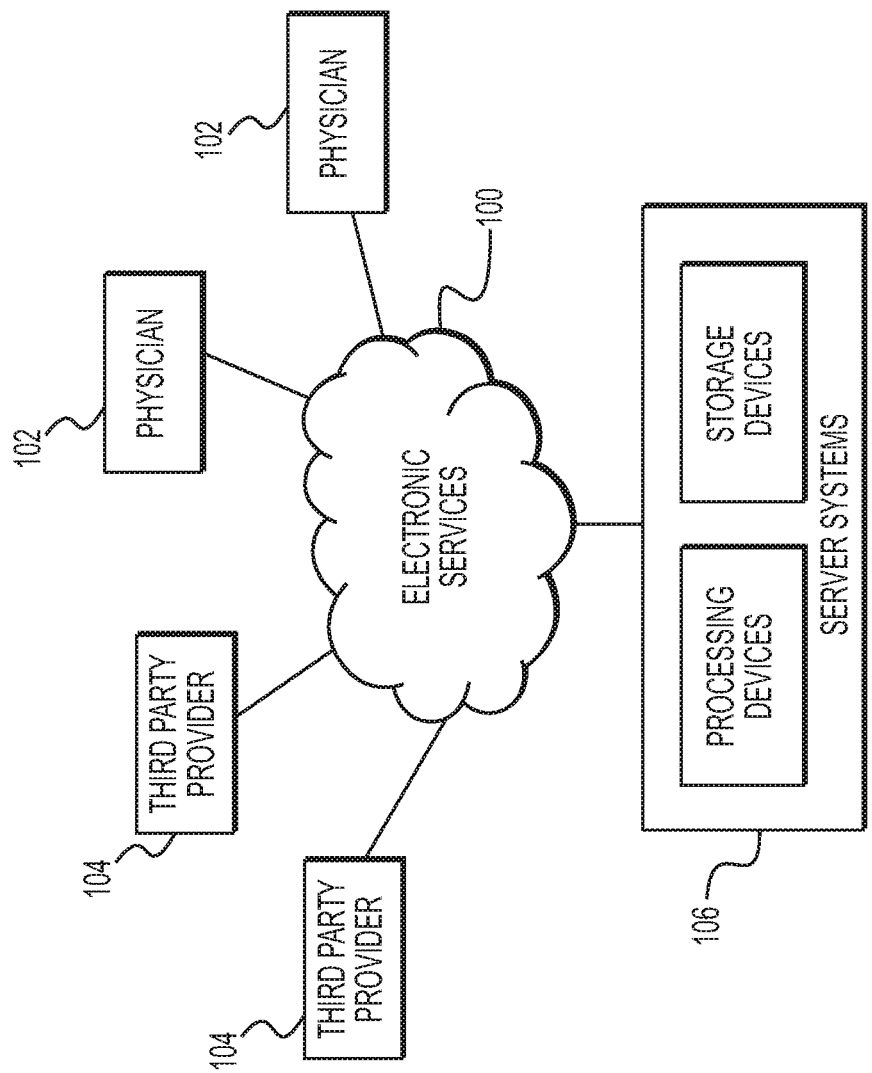
FIG. 1 is a block diagram of an exemplary system and network for assessing risk of disease, according to an exemplary embodiment of the present disclosure.

Reference will now be made in detail to the exemplary embodiments of the invention, examples of which are illustrated in the accompanying drawings. Wherever possible, the same reference numbers will be used throughout the drawings to refer to the same or like parts.

CFD simulations have been successfully used to predict spatial and temporal variations of flow rate and pressure of blood in arteries, including FFR. Alternatives to FFR may include evaluating flow rates in order to infer the functional significance of stenoses. The alternatives may serve to replace, verify, compliment, and/or supplement conclusions based on FFR. Flow rate metrics that may measure functional significance of stenosis include, for example, transluminal attenuation gradient (TAG), corrected thrombosis in myocardial infarction frame count (CTFC), thrombolysis in myocardial infarction myocardial perfusion grade (TMPG), and corrected coronary opacification (CCO). These exemplary metrics may be developed to evaluate severity of stenoses, either as standalone metrics, or as compliments to each other and/or to other measurements (e.g., FFR). Metrics may compliment another, e.g., where a TAG score supplements a finding in $FFR_{CT}$ or $FFR_{CT}$ is consistent with a finding based on a TAG score. Essentially, the metrics present multiple ways to assess likelihood of heart disease. Therefore, one metric may offer an assessment, and using multiple measures or scores may reinforce, verify, and/or clarify the assessment.

TAG, CTFC, TMPG, and CCO involve analyzing flow rates, meaning experimental data is derived from images of contrast agents traveling through blood vessels. Using TAG, CTFC, TMPG, and/or CCO to calculate functional severity may be based on the notion that blood flow velocity may increase at a stenosis. Due to the increased velocity, contrast agent released in the blood stream may be washed away faster downstream of a stenosis. Contrast agent washing away quickly due to higher velocity near a stenosis may be connected to a low luminal intensity and therefore, a low attenuation gradient, low frame count, or greater corrected coronary opacification differences. Abnormal flow may also contribute to lower TIMI myocardial perfusion grades (TMPG). In this way, TAG, CTFC, TMPG, and/or CCO may be related to stenosis severity. However, limitations in image acquisition in relation to contrast agent flow rates translate to limitations in reliability of experimental TAG scores, CTFC, TMPG, and CCO in providing assessments on severity of stenosis. Therefore, a need exists for improving measurements of TAG scores, CTFC, TMPG, and CCO. The following disclosure is directed to employing blood flow simulations with virtual contrast agent(s) in order to improve TAG score, CTFC, TMPG, and CCO analysis, thereby permitting evaluation of functional significance of stenoses based on TAG, CTFC, TMPG and/or CCO data. The following discussion describes each of the metrics TAG, CTFC, TMPG, and CCO in more detail.

TAG is sometimes characterized as the slope of a linear regression fit between luminal intensity and axial distance. In other words, TAG may be the rate of decrease in luminal intensity per unit distance. As discussed above, TAG may have the potential to serve as an indication of functional severity of stenoses. TAG may be computed by calculating and/or analyzing contrast concentration along an artery of interest and measuring a gradient in the region of interest along the artery. In this way, a TAG score may be inversely proportional to severity of a stenosis. A lower TAG score may indicate a higher degree of stenosis (due to higher velocity blood flow near the stenosis), while a higher TAG score may indicate a low degree or absence of stenosis (due to normal or expected blood flow rate near the stenosis). TAG score may be added to coronary CTA to improve diagnostic accuracy, especially in vessels with calcified lesions.

TAG scores may be measured directly from computed tomography (CT) scans. For example, a TAG score may typically be computed using Hounsfield units calculated across lengths of 5 mm or 10 mm. For instance, a 64-slice coronary computed tomography angiograph (cCTA) may be used to measure radio-density across stenosis in 5 mm length increments, where the difference in radiointensities across measurements may be reported as TAG scores. One study reported that in a cohort of 54 patients, a TAG cutoff of −15 HU/10 mm may predict FFR<=0.8 with a sensitivity of 77%, specificity of 74%, positive predictive value of 67%, and negative predictive value of 86% ("Transluminal attenuation gradient in coronary computed tomography angiography may be a novel noninvasive approach to the identification of functionally significant coronary artery stenosis: a comparison with fractional flow reserve," JACC, 2013). However, another study showed that compared to FFR, sensitivity of TAG scores may be 38%, with an overall accuracy of 67% ("Noninvasive diagnosis of ischemic-causing coronary stenosis using CT angiography: diagnostic value of transluminal attenuation gradient and fractional flow reserve computed from coronary CT angiography compared to invasively measured fractional flow reserve," JACC: cardiovascular imaging, 2012). In other words, while TAG may help evaluate functional severity of stenoses, usage of TAG is still being assessed. Thus, TAG score thresholds are not yet perceived as a common metric, for example, for helping triage patients who are candidates for stenting.

Concerns regarding TAG score are related to (i) insufficient contrast material, especially in distal stenoses, for TAG score analysis to be useful and/or (ii) sufficiency of TAG scores as a standalone metric. Regarding insufficient contrast, while TAG scores measured directly from CT scans may be assumed to be reliable in vessels with good flow rate and sufficient contrast material, the dependence of TAG score on luminal intensity means that distal vessels or vessels with low flow may be prone to substantial errors in direct estimation of TAG score from CT scans. Therefore, a need exists to compensate for limitations relating to TAG scores, especially in relation to distal vessels or vessels with low flow.

In one embodiment, computational prediction of TAG scores may be used to improve accuracy in TAG scores. For example, blood flow simulations may provide theoretical TAG scores, e.g., for distal vessels. In one embodiment, the simulations may include a simulation of virtual contrast agent flowing through a patient-specific model. Advection-diffusion equations for simulated conditions may then yield computationally predicted TAG scores. For instance, advection-diffusion equations may be used to calculate concentration of contrast agent in the arteries of interest. The gradient in concentration profile along lumen centerlines may have one-to-one correspondence with TAG scores. Advection-diffusion equations may include a partial differential equation describing transport of particles in a fluid domain. A variable to solve for in the partial differential equation may include concentration of contrast agent, where velocity of the fluid domain may be calculated by solving the Navier-Stokes equations. Boundary conditions for the partial differential equations may be the contrast concentration at time t=0 (e.g., where the concentration may be based on the amount and location of contrast injection) and conditions at the boundary of the computational domain (where gradient of concentration may be zero). Alternately, arterial walls may also be assumed to be a continuous sink since a network of microvessels may be modeled based on contrast data in proximal vessels with good flow-rate. Diffusivity of contrast agent in the fluid domain may be assumed as a known variable. Alternately, the diffusivity may be calculated using contrast concentration at specific known points and solving an inverse problem.

To improve the use of a TAG score as a standalone metric, improvements to accuracy and versatility of TAG metrics (e.g., using CFD analysis of virtual contrast agent(s)) may permit TAG to operate as a standalone metric. In the interim or in addition, TAG may be used in combination with other hemodynamic parameters to infer functional severity of disease. For example, TAG may be used to compliment CFD simulations and improve the accuracy and/or interpretation of $FFR_{CT}$ (e.g., as calculated in U.S. Pat. No. 8,315,812 filed Jan. 25, 2011, the entire disclosure of which is hereby incorporated by reference herein in its entirety). $FFR_{CT}$ may sometimes fall in an indeterminate zone (e.g., between 0.75 to 0.85 or between 0.7 to 0.9). $FFR_{CT}$ values greater than 0.9 or 0.85 indicate a non-significant stenosis, while values below 0.75 or 0.7 may indicate a functionally significant stenosis. However, if a $FFR_{CT}$ value is between 0.75-0.85 or 0.7-0.9, it may be unknown in some cases whether a lesion is functionally significant. Therefore, a desire exists to improve diagnostic evaluation of $FFT_{CT}$ in the indeterminate zone.

As previously discussed, TAG scores may be calculated based on simulations, for instance, by solving an advection-diffusion equation of virtually simulated contrast agent flow. Using the calculated simulations, a TAG threshold score may be determined and assigned based on a score that optimally predicts functionally significant lesions. For example, a comparison of simulated TAG scores to FFR may provide insight into threshold TAG scores associated with various levels of functional severity of stenoses. Therefore, in vessels where $FFR_{CT}$ is in an indeterminate zone, a TAG score may be evaluated relative to a TAG threshold score. Depending on the comparison, an assessment may be made as to whether a disease is functionally significant. For example, if $FFR_{CT}$ is 0.82, functional significance of the stenosis by $FFT_{CT}$, alone, may be indeterminate. However, if $FFR_{CT}$ is 0.82 and a TAG threshold score is −15 Hounsfield units/10 mm, a TAG score of −25 Hounsfield units/10 mm may prompt the inference that a vessel is, indeed, diseased. In one embodiment, a machine learning algorithm may map $FFT_{CT}$, TAG scores, flow rates, and other features used to measure FFR. Based on the algorithm, a hybrid $FFR_{CT\text{-}TAG}$ value may be calculated, where the $FFR_{CT\text{-}TAG}$ value may have a higher diagnostic accuracy than $FFT_{CT}$ (consistent with U.S. application Ser. No. 13/895,893 filed May 16, 2013, the entire disclosure of which is hereby incorporated by reference herein in its entirety).

Regarding CTFC, CTFC may refer to the number of (imaging) frames passed for contrast agent dye to attenuate to a certain degree or concentration, or for the contrast agent to reach standardized landmarks in portions of vessels, distal from a point of contrast agent injection. The time elapsed for the contrast agent to attenuate or reach the landmarks may serve as indication of functional significance of stenoses. As discussed previously, blood flow velocity may increase in the area of a stenosis, so timing based on CTFC is related to flow rate of a contrast agent, and consequently, severity of a stenosis. Embodiments relating to CTFC may also be applied to other Thrombolysis in Myocardial Infarction (TIMI) derivative measures (e.g., TIMI Myocardial Perfusion Grade (TMPG)).

TMPG is a measure of flow through the myocardium (i.e., myocardial perfusion). While TAG, CTFC, and CCO may relate to coronary artery flow, analysis of TMPG may be derived from measuring myocardial perfusion, e.g., by observing a contrast agent passing through myocardial capillaries. On a coronary angiogram, for example, the contrast agent may be observed, such that imaged myocardium may appear with "blush" indicating the flow of the contrast agent. The TMPG may quantify this "blush." For example, TMPG includes scores 0-3, with 0 being a failure of contrast agent perfusion (e.g., no or minimal blush). A TMPG of 3 indicates normal perfusion, where there is a "blush" appearance in the myocardium and washout of the dye, as expected, after three cardiac cycles. TMPGs less than 3 may indicate abnormal or problematic flow.

CCO is a measure typically used to normalize flow measurements. CCO may be calculated as the quotient of coronary segment intraluminal Hounsfield value (HU) divided by the intraluminal HU taken at the descending aorta. In some cases, the HU is the mean HU, and HU is based on images taken in the same axial plane for both the coronary segment and the descending aorta. In some embodiments, using this quotient may help normalize, for example, TAG scores and CTFC, since TAG and CTFC data is susceptible to transluminal attenuation attributable to imaging (e.g., gating), rather than flow. CCO may correct for transluminal HU lost due to the imaging process. Meanwhile, a CCO difference may also serve as a standalone metric for evaluating severity of stenoses. A CCO difference may be calculated by subtracting a CCO measured from a location proximal a stenosis, from a CCO measured at a location distal to a stenosis. In other words, the CCO difference may be a CCO post-stenosis, subtracted from CCO pre-stenosis. The CCO difference may be higher for vessels with significant stenoses, than vessels with insignificant stenoses. As described before, this may be because contrast agent may wash out more quickly where a stenosis is significant, thus leading to a larger difference in radiodensity (e.g., HU) between CCO pre-stenosis and CCO post-stenosis.

In summary, while TAG scores, CTFC, TMPG, and CCO have the potential to noninvasively indicate functional severity of stenosis, the reliability of these metrics for predicting severity of stenosis may be improved. Therefore, the present disclosure is directed to a method for computationally calculating TAG scores, CTFC, TMPG, and/or CCO using virtual contrast agent flow simulations. Furthermore, the present disclosure is directed to a method for determining ranges or particular scores for comparing or confirming conclusions drawn from different metrics. For example, the present disclosure is directed to a method of determining a TAG threshold score such that calculated TAG scores may be used to complement hemodynamic parameters (e.g., FFR) to better evaluate functional significance of stenoses.

Referring now to the figures, FIG. 1 depicts a block diagram of an exemplary system and network for using virtual contrast agent concentrations and CFD to compute functional significance of stenoses. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

Figure 2A:
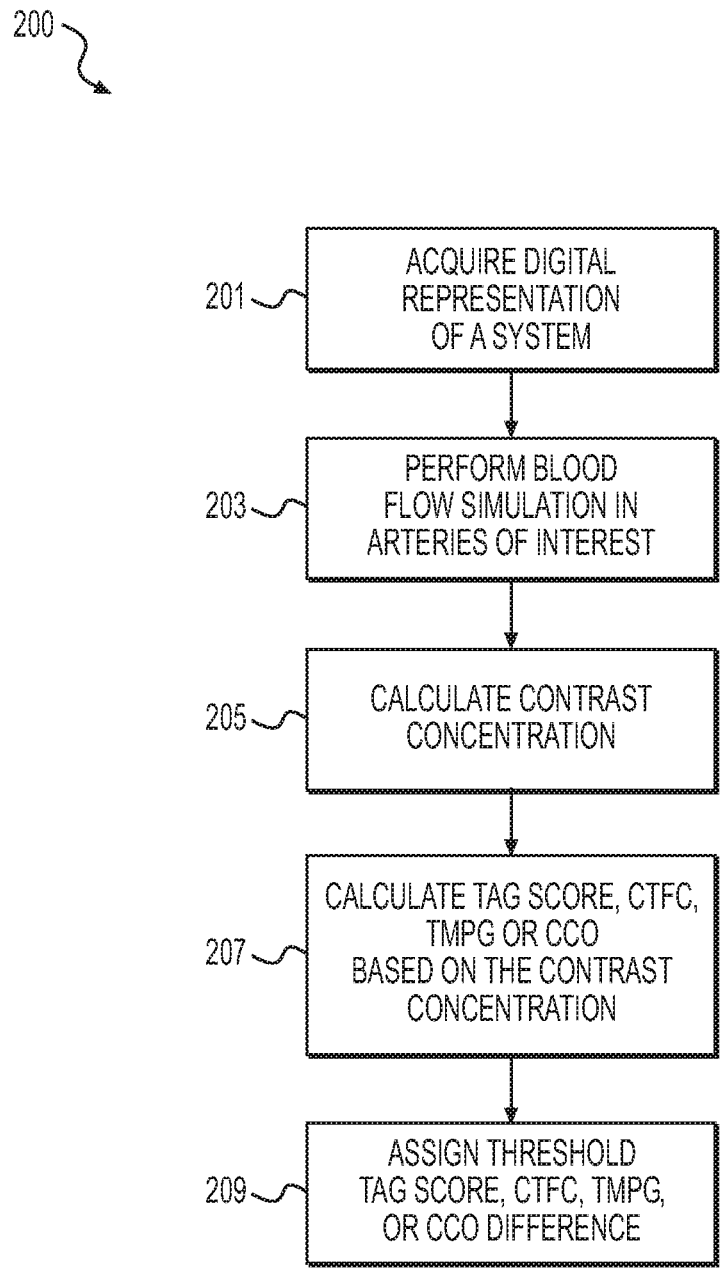
FIG. 2A is a block diagram of an exemplary method of assessing risk of disease using a simulated virtual contrast agent flow simulation, according to an exemplary embodiment of the present disclosure.

FIG. 2A is a block diagram of an exemplary method 200 of assessing risk of disease using a simulated virtual contrast agent flow simulation, according to an exemplary embodiment. In some instances, method 200 may be used for assessing risk of heart disease. In one embodiment, step 201 may include acquiring a digital representation of a system. For example, step 201 may include acquiring a digital scan encompassing a biological or other fluid system that is to be studied. The digital scan or representation may include an image-based representation, measured variables, a list or table of parameter values and feature representative of the system, or a combination thereof. The representation and accompanying data may be loaded from an electronic storage device (e.g., hard drive, RAM, network drive, etc.) into a computational device (e.g., computer, laptop, etc.) used to perform each of the following steps. In one embodiment, step 201 may further include isolating a system of interest. For example, a system of interest may be isolated by delineating a geometry, system properties, and/or specific conditions (e.g., a section of a vessel, geometric parameters associated with the section, and/or a hyperemic state). This aspect of step 201 may encompass additional steps, for example, steps for image processing and reconstructing the system from a raw, received image (e.g., the digital representation of the system of interest) such as in U.S. Pat. No. 8,315,812 which is incorporated by reference.

Step 203 may include performing blood flow simulations using virtual contrast agents in the arteries of interest. In one instance, step 203 may include using clinical variables and a reconstructed image from step 201 to assign lumped parameter boundary conditions that model resistance of micro-vessels. Then, step 203 of performing simulations may include solving Navier-Stokes equations to evaluate pressure and velocities throughout the computational model. Step 203 may further include post-processing the simulation. For example, post-processing may be used to calculate variables for predicting disease. In one such scenario, variables may be compared to reference pressures and flow rates for disease predictions. In some cases, post-processing may involve aggregating and integrating blood pressures and flow-rates along vessels of interest. Disease may be calculated by comparing the aggregated or integrated blood pressures and/or flow rates to reference values, e.g., aortic pressure considered to be normal or healthy, and where the ratio of local to aortic blood pressure yields FFR. Post-processing may also involve mapping a metric on the surfaces of the reconstructed model and outputting a resulting graphical figure.

Step 205 may include calculating contrast concentration. For example, contrast concentration may be determined by solving an advection-diffusion equation. In one embodiment, step 205 may include assigning initial conditions. For example, step 205 may include assigning a known value of virtual contrast concentration near a source location, where contrast is typically injected prior to imaging. The amount of virtual contrast may be patient-specific or a value based on an average from a population of patients. To model diffusivity for calculating contrast concentration, step 205 may include understanding and determining properties of diffusivity through blood flow. For example, for a two-phase system of contrast agent in blood, diffusivity may depend on density of two mediums (e.g., the contrast agent and blood), as well as viscosity of blood. While an amount of virtual contrast may be inferred from a population-based average amount, diffusivity may only be patient-specific. Properties of blood, including diffusivity (and by extension, viscosity), may change based on aggregation of red blood cells. For example, red blood cells may display unique mechanical properties, in which the cells may clump (e.g., aggregate). Tendencies in patients' blood for red blood cell aggregation may be associated with blood sheer rate, which may correspond to viscosity of blood. Using an inverse problem, diffusivity may be inferred directly from contrast concentration in proximal vessels with good flow.

In one embodiment, solving an advection diffusion equation for contrast concentration may include using velocities (e.g., in the form of velocity fields) calculated in step 203. For instance, applying velocity data and initial conditions to advection diffusion equations may yield contrast concentration by way of advection of virtual contrast agent as time progresses.

In one embodiment, step 207 may include calculating (CFD-derived) TAG scores, CTFC, TMPG, or a combination thereof. For example, step 207 may include using contrast agent concentration across lumen centerlines to calculate local gradients. The local gradients may then be mapped to Hounsfield units/mm by multiplying the gradients by a constant. In one embodiment, step 207 may further include accounting for corrected coronary opacification (CCO) in calculating TAG and/or CTFC scores. Further description of this calculation is provided in FIG. 2B.

In one embodiment, step 209 may include assigning a TAG threshold score and/or threshold CTFC, TMPG, or CCO difference. For example, step 209 may be based on a database of patient information associated with a disease or risk of a disease. In some cases, determining an optimal TAG threshold score may include using a least squares error metric to identify patients at risk of a disease. Some scenarios may involve a training database and/or a training TAG score calculating algorithm that may dynamically determine and/or adjust a TAG threshold score according to collected patient information.

Figure 2B:
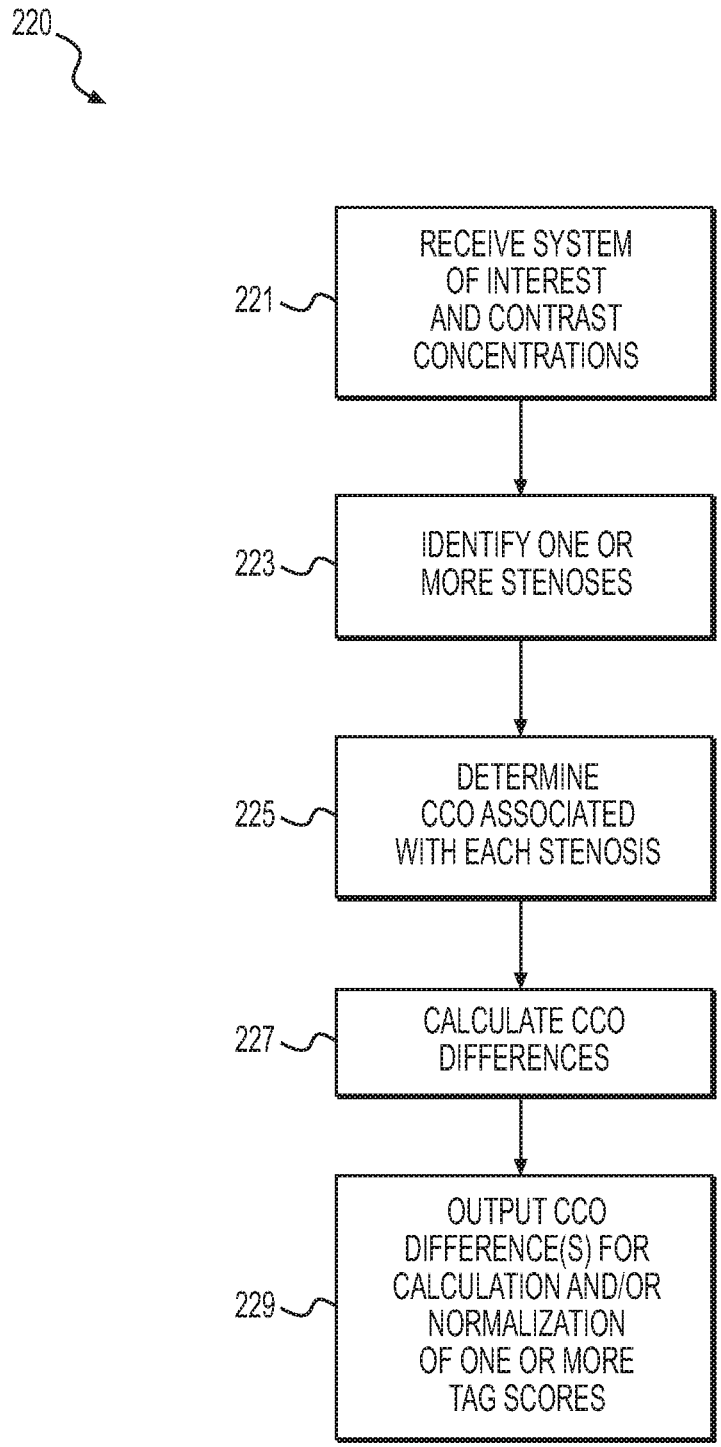
FIG. 2B is a block diagram of an exemplary method of correcting TAG scores using CCO, according to an exemplary embodiment of the present disclosure.

FIG. 2B is a block diagram of an exemplary method 220 of correcting TAG scores using CCO, according to an exemplary embodiment. While CCO may be used to correct TAG scores in this exemplary embodiment, any flow-related metric that may be determined from a flow simulation (e.g., a virtual contrast agent flow simulation) may be used to correct, supplement, or verify a risk assessment. While some assessments may focus on either CTFC, TMPG, TAG, or CCO, other assessments may employ various combinations of the metrics. Method 220 is an exemplary embodiment, focusing on a combination including TAG and CCO.

Imaging of the heart often includes acquiring images throughout or during multiple cardiac cycles. Therefore, in addition to typical variability between separate images, factors caused by cardiac cycles (e.g., timing, cardiac output, bolus geometry, etc.) may contribute to contrast attenuation between various acquired images of coronary arteries. CCO may calculate variations in contrast attenuation caused by different cardiac cycles. Since TAG scores may be based on contrast attenuation (e.g., decrease in luminal intensity per unit distance), taking into account CCO may help to normalize TAG scores. In some instances, failing to normalize contrast attenuation (e.g., using CCO) may result in data where worsening stenosis does not necessarily display a relationship with contrast attenuation. Therefore, step 207 of method 200 may include and/or prompt method 220 in order to strengthen associations between TAG and functional severity of stenoses.

In one embodiment, CCO applies to each "slice" or image in a scan, where CCO may be calculated as, CCO=coronary artery $HU$/aorta($HU$).

Furthermore, a difference in CCO across stenoses may be calculated, wherein a CCO difference may be calculated as, CCO difference=pre-stenosis CCO−post-stenosis CCO.

In one embodiment, step 221 may include receiving a system of interest (e.g., from step 201) and calculated contrast concentrations from a simulation (e.g., from step 205). Step 223 may include identifying one or more stenoses within the system of interest. Step 225 may include determining, for each stenoses, a pre-stenosis CCO and a post-stenosis CCO. For example, step 225 may include defining pre-stenosis and post-stenosis CCO to be the minimum CCO ($CCO_{min}$) at locations pre-stenosis and post-stenosis, respectively. Step 225 may further include calculating and/or receiving CCO values (e.g., $CCO_{min}$). Step 227 may include calculating CCO differences, for example, CCO differences across each of the determined stenoses.

Figure 2C:
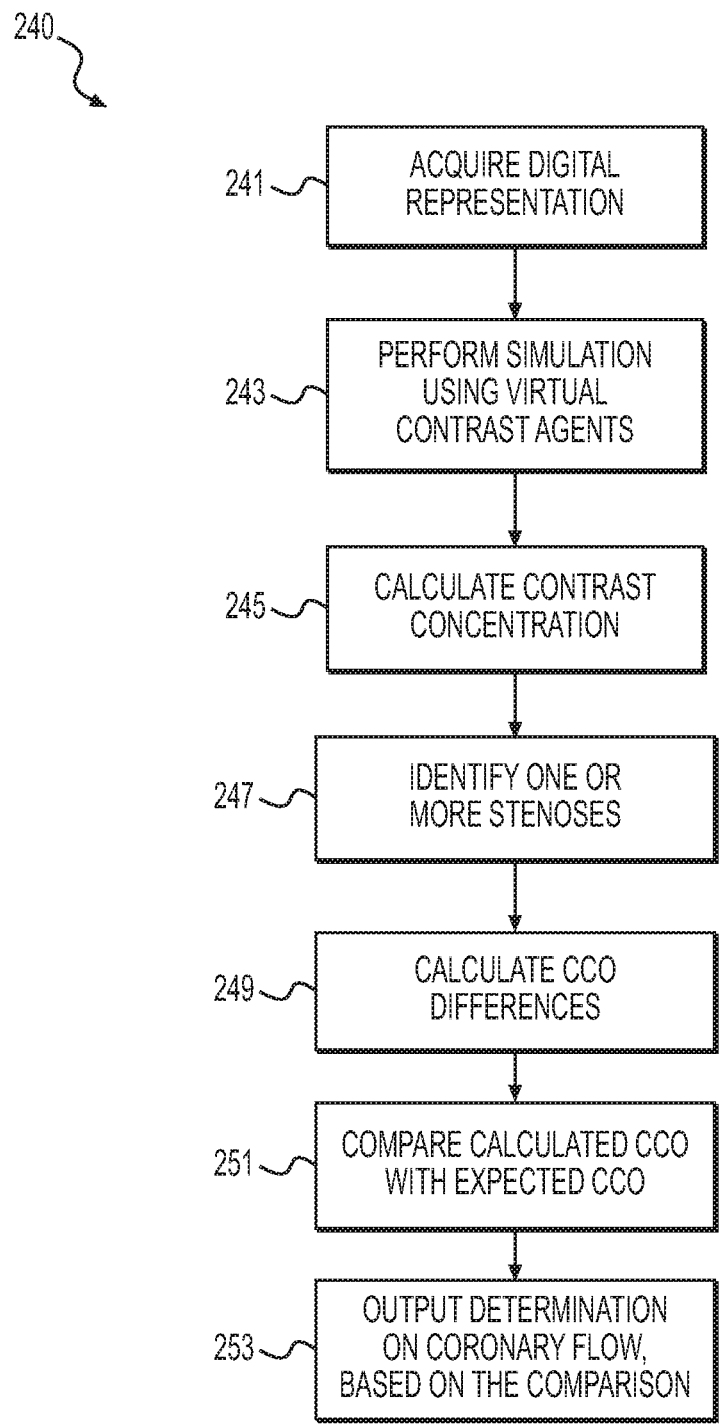
FIG. 2C is a block diagram of an exemplary method of calculating CCO, according to an exemplary embodiment of the present disclosure.

Once CCO differences are calculated, the CCO differences may be used in various ways. In one embodiment, CCO differences may be used to evaluate coronary blood flow. For instance, CCO differences across one or more stenoses may be analyzed collectively to make inferences on blood flow through the modeled system of interest. FIG. 2C provides further detail of such an application of CCO differences. In another embodiment, CCO difference for each stenosis may provide an indication of a severity of a coronary stenosis. In addition, CCO difference may be combined with another metric to evaluate severity of a coronary stenosis. For example, step 229 may include outputting CCO calculations (from step 225) and/or CCO difference calculations (from step 227) to an entity calculating TAG scores (e.g., an entity performing method 200, and more specifically, step 207). Alternately, step 229 may include identifying a metric and correcting or normalizing the metric based on the CCO and/or CCO differences. In other words, CCO may be calculated using computational means to normalize or improve TAG scores derived from imaging. Further, the normalized and/or improved TAG scores may be used to refine $FFR_{CT}$ analyses.

FIG. 2C is a block diagram of an exemplary method 240 of calculating CCO, according to an exemplary embodiment. In some embodiments, CCO may estimate coronary blood flow, independent of TAG. Steps 241-245 may be similar to steps 201-205, since these steps provide the data from which flow rate simulations (and consequently, evaluation of stenoses) may be derived.

In one embodiment, step 241 may include acquiring a digital scan and/or reconstruction of a system of interest. For example, the data may be loaded from an electronic storage device into a computational device. Step 241 may further include delineating a specific geometry, a set of system properties, and/or specific conditions for an analysis. Step 243 may include performing blood flow simulations, for instance, through particular arteries of interest. This step may include evaluating pressure and velocities throughout a computational model made based on the geometries of the representation(s) provided in step 241. Step 245 may include calculating virtual contrast concentration for flow through the model based on the simulations. In one embodiment, step 247 may include identifying coronary stenoses within the model, where step 249 may include calculating CCO differences across the stenoses. In one embodiment, mean CCO may be known to approach 1.0 (e.g., CCO=0.979±0.070) for "normal" arteries with normal blood flow. This CCO may be denoted as, an "expected CCO." Step 251 may include comparing calculated CCO with expected CCO and/or determining whether calculated CCO deviates from expected CCO. Step 253 may include outputting a determination of abnormal or normal resting coronary flow, based on the comparison of calculated CCO versus "normal" CCO.

Figure 3:
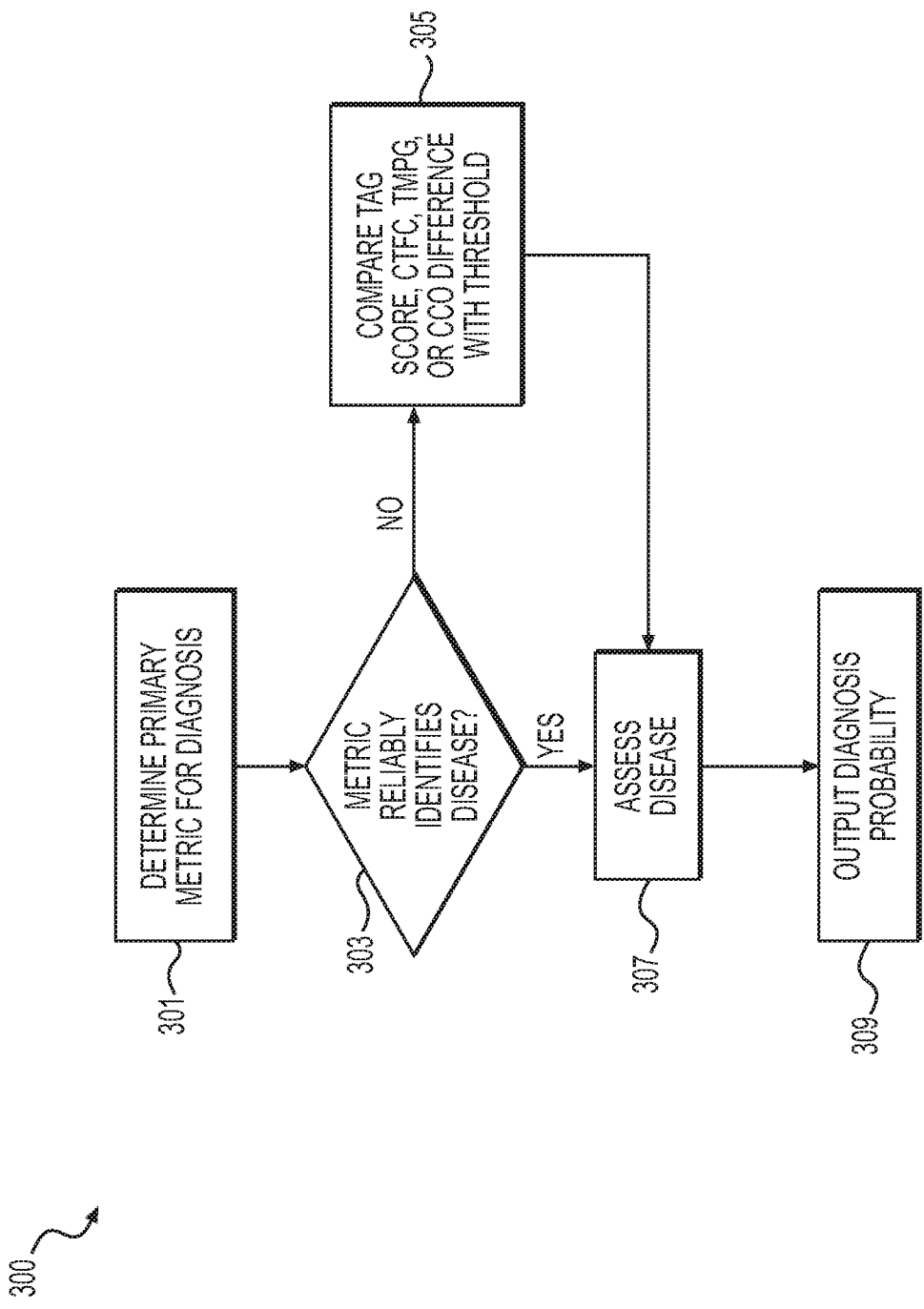
FIG. 3 is a block diagram of an exemplary method of enriching a hemodynamic metric with one or more measurements from the virtual contrast agent simulation to assign diagnoses, according to an exemplary embodiment of the present disclosure.

FIG. 3 is a block diagram of an exemplary method 300 of enriching hemodynamic metrics (e.g., $FFR_{CT}$) using measurements from the virtual contrast agent simulation in order to refine or improve diagnoses, according to an exemplary embodiment. In one embodiment, step 301 may include determining a primary metric for diagnosis. For example, a primary metric may include a disease-specific hemodynamic metric (e.g., $FFR_{CT}$). Other instances of primary metrics may include coronary flow reserve or coronary flow velocity reserve, for example. As previously discussed, some embodiments may include TAG as a "primary" metric and another hemodynamic metric as secondary or supplemental. For instance, TAG may be a primary metric, and $FFR_{CT}$ a supplemental metric. Essentially, the metrics all assess likelihood of heart disease. Using multiple measures or scores serves to reinforce and/or verify assessments.

In some embodiments, step 301 may include selecting a primary metric from a collection of metrics for diagnosis. The selection may be based on the disease, patient information, and/or averaged patient population information, etc. Step 303 may include causing a determination of whether the hemodynamic metric may reliably identify a disease and/or distinguish a disease from another disease. If the hemodynamic metric is insufficient to determine a disease, step 305 may be prompted, where step 305 may include evaluating a TAG score, CTFC, TMPG, and/or CCO. For example, step 305 may include comparing a TAG score, CTFC, TMPG, and/or CCO with a threshold TAG score, CTFC, TMPG, and/or CCO, respectively. Step 305 may include employing the metrics, TAG, CTFC, TMPG, and CCO individually, all together, or in any combination. Step 307 may include inferring and/or determining that a vessel of interest is diseased, based on the comparison of step 305 (e.g., whether the TAG score exceeds or falls below the threshold TAG score) and the determined primary metric. The determination of step 307 may be based on information regarding blood particles' flow along arteries, along with hemodynamic variables. In some instances, the determination in step 307 may include a probability that the vessel is diseased or a probability of the likelihood of the diagnosis being correct. In one embodiment, step 309 may include outputting the diagnosis probability to an electronic storage medium (e.g., a hard disk, RAM, network drive, user display, etc.).

Figure 4:
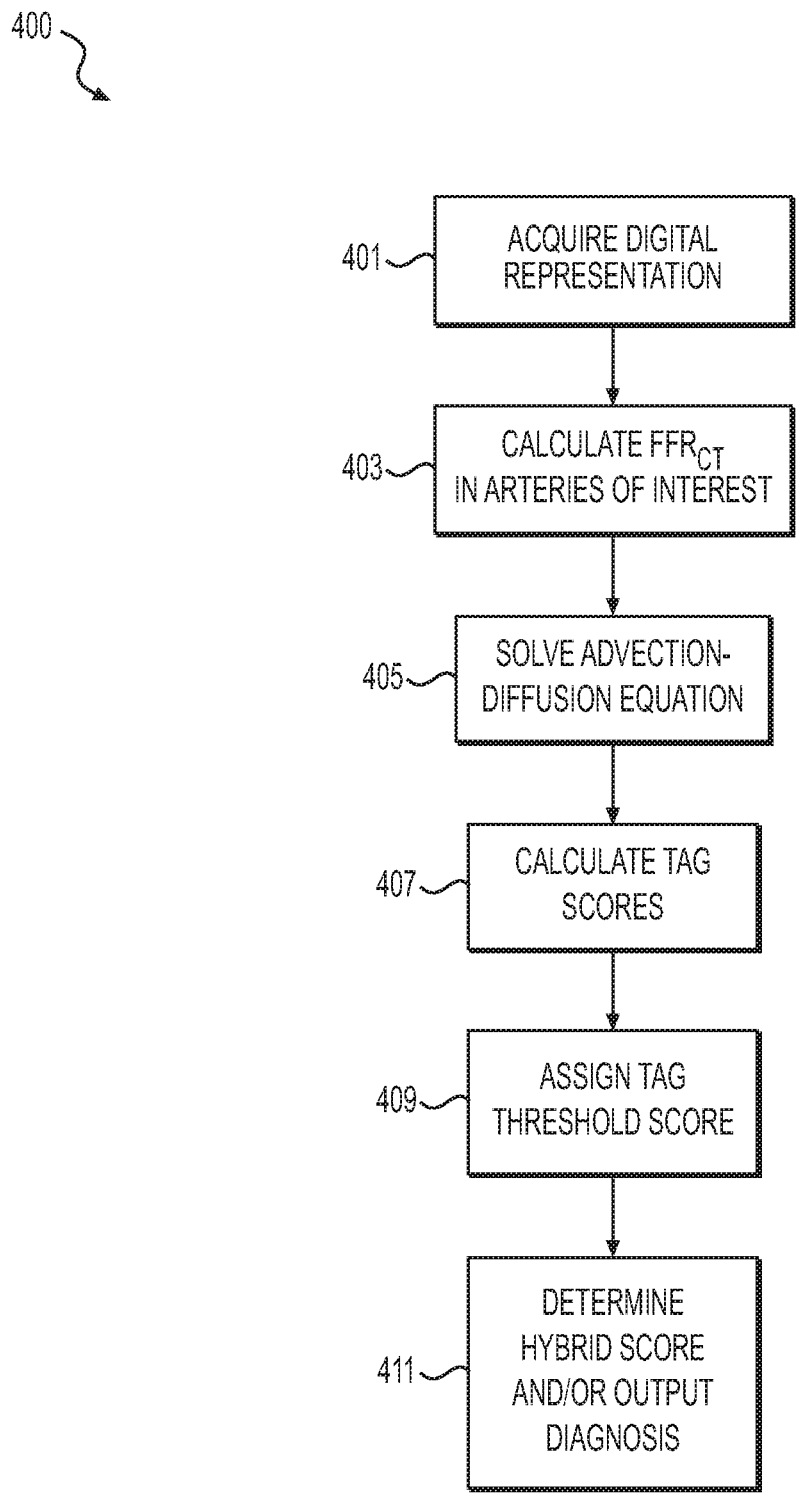
FIG. 4 is a block diagram of an exemplary method for assessing a severity of a stenosis based on a TAG score calculated using a blood flow simulation of a virtual contrast agent, according to an exemplary embodiment of the present disclosure.

FIG. 4 is a block diagram of an exemplary method 400 of a specific embodiment for assessing severity of a stenosis based on a TAG score calculated using a blood flow simulation with a virtual contrast agent, according to an exemplary embodiment. In other words, method 400 is a specific embodiment employing method 200 and 300 of determining a TAG score, and then using the TAG score to assess risk of heart disease. In one embodiment, step 401 may include acquiring and processing input data. For example, step 401 may include, for one or more patients, acquiring a digital representation (e.g., the memory or digital storage (e.g., hard drive, network drive) of a computational device such as a computer, laptop, DSP, server, etc.) of an image scan of a patient, a digital representation including regions of interest, clinical parameters, and a set of derived quantities calculated from the image scan and the digital representation.

In one embodiment, the image scan of the patient may include the ascending aorta and coronary artery tree. The type of scan may include cardiac computed tomography (CCTA), MRI, ultrasound etc. The digital representation may be based on the image scan of the patient. Furthermore, the digital representation may encompass regions of interest. For example, step 401 may include isolating the regions of interest and/or receiving the digital representation with regions of interest isolated. For instance, centerlines, which pass through the center of vessels of interest, may be computed. The computed centerlines may be used to construct lumen segments manually or automatically, and voxels belonging to the aorta and to the lumen of the coronary arteries may be identified. Based on an identification of relevant voxels, a geometric model of the aorta and relevant coronary arteries may be reconstructed.

In addition to CCTA, the set of clinical parameters may be measured, where the parameters may include heart-rate, systolic and diastolic brachial blood pressures, hematocrit, patient height and weight, and patient history, e.g., smoking status, presence/absence of diabetes, etc. A set of derived quantities may be calculated from the image scan and the digital representation. These derived quantities may include:

Myocardial mass ($m_{myo}$), which may be obtained by image segmentation of the left ventricle. For instance, the segmentation may be used to calculate the volume of myocardium, where multiplying the volume of the myocardium with a blood density may yield the myocardial mass.

Body surface area, which may be calculated from the patient height (h) and weight (w) as $$BSA = \sqrt{\frac{hw}{3600}}.$$

Viscosity, which may be calculated from the hematocrit (hem) as $$\eta = \frac{c}{\left(1 - \frac{hem}{100}\right)^{2.5}}$$

where c is 0.0012.

Inlet aortic flow rate (Q), which may be calculated from scaling studies as $$Q = \frac{1}{60} BSA^{1.15}$$

Coronary flow rate ($q_{cor}$), which may be calculated from myocardial mass as $$q_{cor} = c_{dil} \frac{5.09}{60} m_{myo}^{0.75}$$

where $c_{dil}$ may be the dilation factor.

Coronary resistance, where the net coronary resistance may be calculated from the desired coronary flow, and the value for individual outlets may be calculated based on their areas.

Resistance of outlet aorta, which may be calculated based on aortic pressure, aortic flow rate, and desired coronary flow rate.

In one embodiment, step 403 may include calculating FFR$_{CT}$ in arteries of interest. For example, step 403 may include calculating FFR values for each patient that underwent CCTA. For instance, FFR values may be calculated by solving Navier-Stokes equations. More specifically, step 403 may include discretizing the arteries of interest into finite elements, using the measured aortic pressure at the aortic inlet of the computational model and using resistances (e.g., coronary resistance(s) calculated in step 401) at all of the outlets. The resulting set of equations after discretization may be solved to calculate blood velocity and pressure at all of the discretized nodes.

In one embodiment, step 405 may include solving an advection-diffusion equation. A general advection diffusion equation may include a set of sources and a set of sinks, where solving the advection diffusion equation may involve solving for concentration in the rest of the domain. For step 405, a basic embodiment may include using one source (e.g., a location where contrast is injected). Some embodiments may include advection diffusion equations with multiple sources, for instance, where contrast agent may be injected in the computational domain or geometry. In some cases, the computational model may not include injection location. In one embodiment, a two-phase system comprised of the virtual contrast agent and blood, may be given by the advection diffusion equation:

$$\frac{\partial c}{\partial t} = \nabla \cdot (D \nabla c) - \nabla \cdot (vc)$$

where v may be the velocity of blood, c may be the concentration of contrast, and D may be the diffusivity of contrast agent in blood. In one embodiment, step 405 may further include assigning boundary conditions, modeling diffusivity, and then solving the advection-diffusion equation based on the boundary conditions and modeling. Regarding boundary conditions, the concentration of the contrast agent at time t=0, across lumen at the ostia (o), may be c(x=ostium, t=0)=$c_0$. Since blood velocity at walls of the artery may be modeled as zero, a gradient of concentration at vessel walls in a direction normal to the wall may be imposed to be zero. The same boundary condition may be used at the truncated coronary boundaries.

Regarding modeling diffusivity, values for molecular diffusivity of, for example, Gadolinium based contrast in blood has been reported in literature. However, these values may change based on temperature, rheological properties of blood, etc. Hence, step 405 may include calculating a patient-specific diffusivity by using a contrast concentration directly from one or more CCTA scans, and solving an inverse problem to calculate diffusivity. The inverse problem may involve solving the following optimization problem:

$$\hat{D} = \arg\min_D (c(D) - c_{meas})^2$$

where $c_{meas}$ may be measured contrast concentration at proximal locations close to the ostium (e.g., locations picked so that concentration may be reliably inferred from intensity of images).

Regarding solving the advection-diffusion equations, advection-diffusion equations may be discretized in space using the same computational mesh as used to solve Navier-Stokes equations (e.g., from step 403). A finite difference scheme may be used to discretize the equations in time. Hence, by starting from the initial conditions and solving the discretized equations sequentially, contrast concentration may be calculated throughout the arteries of interest.

In one embodiment, step 407 may include calculating CFD-derived TAG scores. For example, step 407 may include calculating transluminal gradients using a linear regression on the contrast concentration along lesions. While these gradients may have one-to-one correspondence with TAG, the gradients may not be identical since TAG may use radiointensity measured in Hounsfield units. A scaling factor may be used to convert concentration gradient into TAG scores. For example, TAG scores at specific measurement locations (e.g., locations where contrast concentration was measured for step 405) may be used as references for the scaling factor.

In one embodiment, step 409 may include assigning a TAG threshold score. In one embodiment, a TAG threshold score may be computed by calculating the TAG coefficient on a database of patients with measured FFR and calculating a TAG threshold score ($T_c$) having the best diagnostic accuracy. For example, step 409 may employ the following equation:

$$\hat{T}_C = \arg\min_{T_C}(I(TAG - T_C) - I(FFR - 0.8))^2$$

In one embodiment, step 411 may include determining a hybrid score and/or providing a diagnosis. In one embodiment, step 411 may include using the calculated TAG score, and threshold TAG score may be used as standalone metrics to assess risk of heart disease. Alternately, step 411 may include using FFR$_{CT}$ as a primary diagnostic tool. In such an embodiment, a calculated TAG score may be used if FFR$_{CT}$ lies in an indeterminate region. In a further embodiment, TAG score and FFR$_{CT}$, along with blood flow rate and geometric disease burden may be used as features in a machine learning algorithm, where the algorithm may be used to calculate a regressor that maps these values to an hybrid FFR$_{CT-TAG}$ value. TAG and a profile of a contrast agent to improve upon a machine learning algorithm.

Various embodiments of the present disclosure relate generally to assessing risk of heart disease, specifically, using virtual contrast flow simulations to improve noninvasive metrics based on flow rate. For example, the present disclosure includes calculating TAG, CTFC, TMPG, and/or CCO to infer functional significance of a stenosis. Some instances may include determining thresholds associated with the metrics, where calculations falling above or below the thresholds indicate likelihood of heart disease. Furthermore, some instances may include creating hybrid metrics to improve reliability of assessments overall.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of determining blood flow metrics, the method comprising:
receiving image data of a patient's vasculature;
identifying, from the image data, one or more voxels and/or pixels associated with the patient's vasculature and identifying a region of interest of the image data;
generating, based on the identified voxels and/or pixels and the region of interest, a patient-specific geometric model comprising a reconstruction of a patient's vasculature;
determining a patient-specific computational model of blood flow using the patient-specific geometric model obtained from the received image data, the patient-specific computational model of blood flow being different from the patient-specific geometric model;
determining at least one simulated patient-specific blood flow metric based on the patient-specific computational model of blood flow and the patient-specific geometric model, wherein determining at least one simulated patient-specific blood flow metric comprises discretizing the patient's vasculature of interest into finite elements based on 1) measured aortic pressure at an aortic inlet of the computational model and 2) calculated coronary resistances;
determining whether the simulated patient-specific blood flow metric is within a range between a non-functionally-significant blood flow metric value and a functionally significant blood flow metric value;
modeling, based on the patient-specific computational model of blood flow in the patient-specific geometric model and at least one of patient temperature and/or patient rheological properties of blood, a diffusivity of one or more virtual contrast agents in blood at a plurality of predetermined points in the patient-specific geometric model;
upon determining the simulated patient-specific blood flow metric is within a range between a non-functionally-significant blood flow metric value and a functionally significant blood flow metric value, determining one or more software simulated transluminal attenuation gradient (TAG) metrics, based on the diffusivity of the one or more simulated virtual contrast agents in blood in the patient-specific geometric, wherein determining one or more software simulated transluminal attenuation gradient (TAG) metrics comprises: assigning a known value of virtual contrast concentration near a source location and assigning values of virtual contrast concentration along lesions of the patient's vasculature, calculating transluminal gradients using a linear regression of the virtual contrast concentration along the lesions of the patient's vasculature, and applying a scaling factor to the virtual concentration gradient to determine a TAG metric score;
providing the simulated TAG metrics and the simulated patient-specific blood flow metric for output, and
determining a risk of heart disease for a patient using the determined TAG metric score and a threshold TAG score, the threshold TAG score being calculated based on a database of patients with measured blood flow metrics.

2. The method of claim 1, further including:
determining a diagnostic flow metric.

3. The method of claim 2, wherein the diagnostic flow metric is fractional flow reserve.

4. The method of claim 1, further including:
determining a landmark of the patient-specific geometric model;
determining a time elapsed for the one or more virtual contrast agents to attenuate or reach the landmark; and
determining a functional significance of a stenosis based on the time elapsed.

5. The method of claim 1, further including:
determining a local gradient across a lumen centerline based on the diffusivity of one or more virtual contrast agents.

6. The method of claim 1, wherein a value of simulated patient-specific blood flow metric values below 0.7 indicates functionally significant simulated patient-specific blood flow metric values, and wherein a value of simulated patient-specific blood flow metric values above 0.9 indicates non-functionally significant simulated patient-specific blood flow metric values.

7. The method of claim 1, wherein a value of simulated patient-specific blood flow metric values below 0.75 indicates functionally significant simulated patient-specific blood flow metric values, and wherein a value of simulated patient-specific blood flow metric values above 0.85 indicates non-functionally significant simulated patient-specific blood flow metric values.

8. A system for determining blood flow metrics, the system comprising:
at least one data storage device storing instructions for assessing risk of disease; and
at least one processor configured to execute the instructions to perform a method including:
receiving image data of a patient's vasculature;
identifying, from the image data, one or more voxels and/or pixels associated with the patient's vasculature and identifying a region of interest of the image data;
generating, based on the identified voxels and/or pixels and the region of interest, a patient-specific geometric model comprising a reconstruction of a patient's vasculature;
determining a patient-specific computational model of blood flow using the patient-specific geometric model obtained from the received image data, the patient-specific computational model of blood flow being different from the patient-specific geometric model;
determining at least one simulated patient-specific blood flow metric based on the patient-specific computational model of blood flow and the patient-specific geometric model, wherein determining at least one simulated patient-specific blood flow metric comprises discretizing the patient's vasculature of interest into finite elements based on, 1) measured aortic pressure at an aortic inlet of the computational model and 2) calculated coronary resistances;
determining whether the simulated patient-specific blood flow metric is within a range between a non-functionally-significant blood flow metric value and a functionally significant blood flow metric value;
modeling, based on the patient-specific computational model of blood flow in the patient-specific geometric model and at least one of patient temperature and/or patient rheological properties of blood, a diffusivity of one or more virtual contrast agents in blood at a plurality of predetermined points in the patient-specific geometric model;
based on determining the simulated patient-specific blood flow metric is within a range between a non-functionally-significant blood flow metric value and a functionally significant blood flow metric value, determining one or more software simulated transluminal attenuation gradient (TAG) metrics, based on the diffusivity of the one or more simulated virtual contrast agents in blood in the patient-specific geometric model, wherein determining one or more simulated transluminal attenuation gradient (TAG) metrics comprises: assigning a known value of virtual contrast concentration near a source location and assigning values of virtual contrast concentration along lesions of the patient's vasculature, calculating transluminal gradients using a linear regression of the virtual contrast concentration along the lesions of the patient's vasculature, and applying a scaling factor to the virtual concentration gradient to determine a TAG metric score;

providing the simulated TAG metrics and the simulated patient-specific blood flow metric for output, and determining a risk of heart disease for a patient using the determined TAG metric score and a threshold TAG score, the threshold TAG score being calculated based on a database of patients with measured blood flow metrics.

9. The system of claim 8, wherein the at least one processor is further configured for:
determining a diagnostic flow metric.

10. The system of claim 9, wherein the diagnostic flow metric is fractional flow reserve.

11. The system of claim 8, wherein the at least one processor is further configured for:
determining a landmark of the patient-specific geometric model;
determining a time elapsed for the one or more virtual contrast agents to attenuate or reach the landmark; and
determining a functional significance of a stenosis based on the time elapsed.

12. The system of claim 8, wherein the at least one processor is further configured for:
determining a local gradient across a lumen centerline based on the diffusivity of one or more virtual contrast agents.

13. A non-transitory computer readable medium for use on a computer system containing computer-executable programming instructions for determining blood flow metrics, the programming instructions, when executed by the computer system, performing a method comprising:
receiving image data of a patient's vasculature;
identifying, from the image data, one or more voxels and/or pixels associated with the patient's vasculature and identifying a region of interest of the image data;
generating, based on the identified voxels and/or pixels and the region of interest, a patient-specific geometric model comprising a reconstruction of a patient's vasculature;
determining a patient-specific computational model of blood flow using the patient-specific geometric model obtained from the received image data, the patient-specific computational model of blood flow being different from the patient-specific geometric model;
determining at least one simulated patient-specific blood flow metric based on the patient-specific computational model of blood flow and the patient-specific geometric model, wherein determining at least one simulated patient-specific blood flow metric comprises discretizing the patient's vasculature of interest into finite elements based on, 1) measured aortic pressure at an aortic inlet of the computational model and 2) calculated coronary resistances;

determining whether the simulated patient-specific blood flow metric is within a range between a non-functionally-significant blood flow metric value and a functionally significant blood flow metric value;

modeling, based on the patient-specific computational model of blood flow in the patient-specific geometric model and at least one of patient temperature and/or patient rheological properties of blood, a diffusivity of one or more virtual contrast agents in blood at a plurality of predetermined points in the patient-specific geometric model;

upon determining the simulated patient-specific blood flow metric is within a range between a non-functionally-significant blood flow metric value and a functionally significant blood flow metric value, determining one or more software simulated transluminal attenuation gradient (TAG) metrics, based on the diffusivity of the one or more simulated virtual contrast agents in blood in the patient-specific geometric model, wherein determining one or more simulated transluminal attenuation gradient (TAG) metrics comprises: assigning a known value of virtual contrast concentration near a source location and assigning values of virtual contrast concentration along lesions of the patient's vasculature, calculating transluminal gradients using a linear regression of the virtual contrast concentration along the lesions of the patient's vasculature, and applying a scaling factor to the virtual concentration gradient to determine a TAG metric score;

providing the simulated TAG metrics and the simulated patient-specific blood flow metric for output, and determining a risk of heart disease for a patient using the determined TAG metric score and a threshold TAG score, the threshold TAG score being calculated based on a database of patients with measured blood flow metrics.

14. The non-transitory computer readable medium of claim 13, the method further comprising:
determining a diagnostic flow metric.

15. The non-transitory computer readable medium of claim 14, wherein the diagnostic flow metric is fractional flow reserve.

16. The non-transitory computer readable medium of claim 13, the method further comprising:
determining a landmark of the patient-specific geometric model;
determining a time elapsed for the one or more virtual contrast agents to attenuate or reach the landmark; and
determining a functional significance of a stenosis based on the time elapsed.

17. The non-transitory computer readable medium of claim 13, the method further comprising:
determining a local gradient across a lumen centerline based on the diffusivity of one or more virtual contrast agents.

* * * * *